United States Patent [19]

Chrisp

[11] 4,179,930
[45] Dec. 25, 1979

[54] GRAIN PROBE

[76] Inventor: Lynn E. Chrisp, R.R.#1, Juniata, Nebr. 68955

[21] Appl. No.: 966,554

[22] Filed: Dec. 5, 1978

[51] Int. Cl.² .............................................. G01N 1/12
[52] U.S. Cl. .................................................. 73/425.2
[58] Field of Search ............... 73/425.2, 421 R, 421 B

[56] References Cited
FOREIGN PATENT DOCUMENTS 1154184  6/1969  United Kingdom .................... 73/425.2

Primary Examiner—Donald O. Woodiel
Attorney, Agent, or Firm—Schmidt, Johnson, Hovey & Williams

[57] ABSTRACT

A long tube serves both as a handle for the probe and a means by which a grain sample can be collected at the lower end of the tube just above the penetrating nose thereof. A laterally disposed port in the tube above the nose provides an entry way for grain into the interior chamber of the tube during taking of the sample, and opening and closing of such port is controlled by a free-sliding sleeve that, when disposed against an upper stop, closes the port and when disposed against a lower stop, opens the port. When the probe is shoved nose-first down into the grain supply, the resistance of the grain surrounding the probe immediately slides the sleeve up against the upper stop so as to maintain the port closed until the probe reaches the desired testing depth, whereupon a slight upward jerk on the probe will cause the grain to shove the sleeve down against the lower stop and thereby open the port and permit a sample of grain to enter the same. After complete removal of the probe from the grain supply, the probe may be inverted so as to pour the sample out of the open end of the probe into an awaiting receptacle.

5 Claims, 7 Drawing Figures

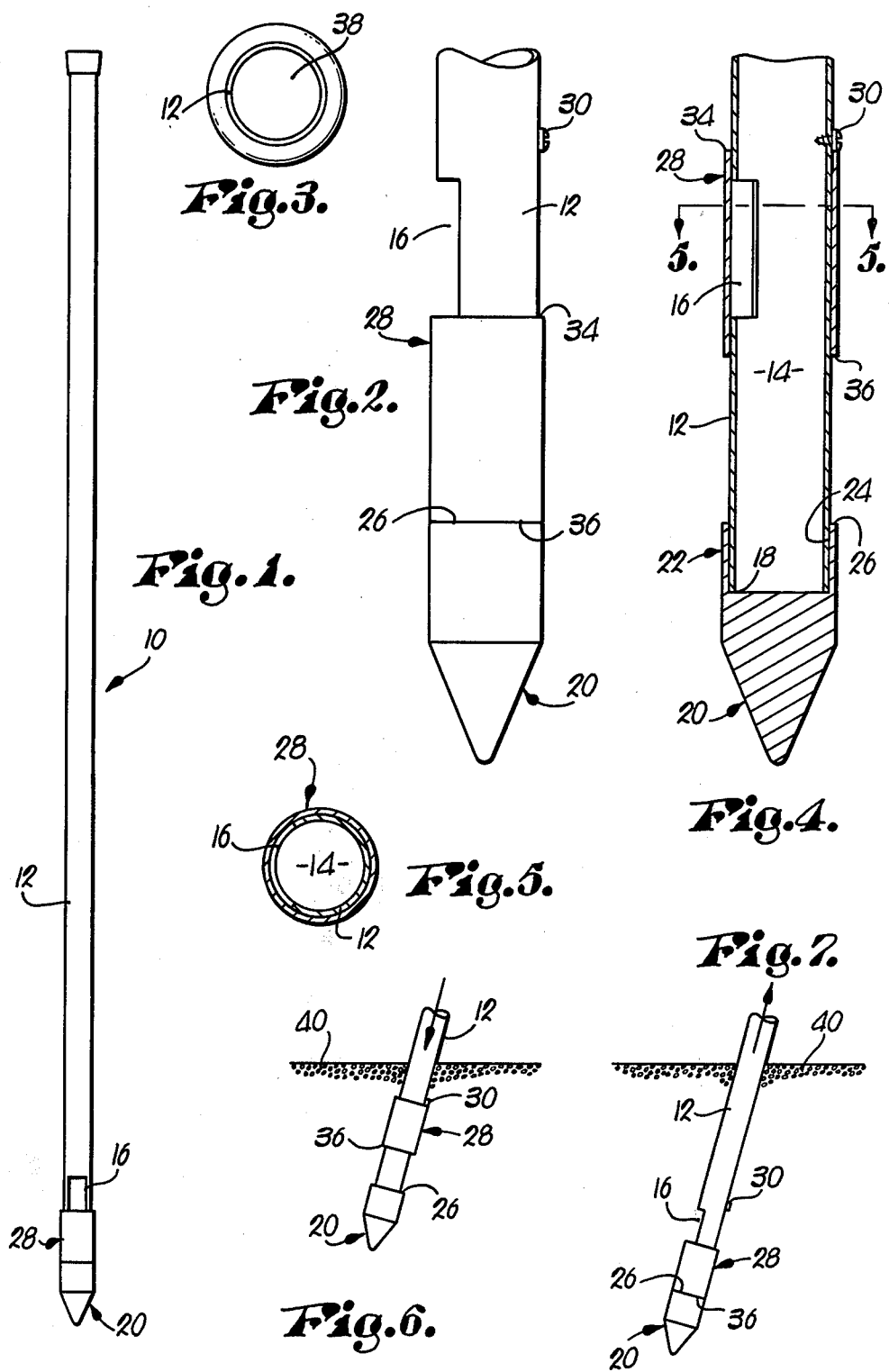

GRAIN PROBE

TECHNICAL FIELD

This invention relates to a tool for use in obtaining a sample of grain at a selected depth in a storage bin or the like for purposes of checking the moisture content of such sample.

BACKGROUND ART

A number of different types of grain sampling tools are presently known to exist. Conventional probes, however, are typically unduely complicated, unwieldy to use, needlessly expensive and are frequently designed to provide more features than actually required by the farmer or other user who periodically takes samples of the moisture content of his stored grain at certain preselected depths.

For example, in some instances the probe consists of a number of separate, unattached components that must be assembled together at the time of use in order to function properly, and such an arrangement has the disadvantage of inviting loss of one or more of the components either during storage or during the sampling operation itself when the user is positioned within the grain storage tank attempting to assemble, use and disassemble the tool.

Additionally, some prior sampling tools have utilized a two-part sampling probe in which the top part, or cap, can be jerked upwardly off the lower sample-receiving part after being thrust down into the grain in a closed condition such that, once separated, a gap will be presented between the cap and the receiving part to permit the entry of the grain sample into the receiving part. Such two parts are commonly connected together with a loose-jointed, hinging strap or the like by which the lower part can be tilted relative to the upper part after withdrawal of the probe from the grain, and such a construction becomes quite unwieldy when attempts are made to thrust the probe down into the grain, because such two parts must be perfectly aligned in order to properly reclose the probe and maintain such closure during downward thrusting into the grain. By the same token, manufacturing costs and the likelihood of mechanical shortcomings are relatively high with this type of construction.

Other sampling tools have provided for the simultaneous sampling of grain at several different levels, and to this end they have utilized a pair of concentrically disposed tubes, the outer of which is provided with a longitudinal series of lateral ports and the inner of which is provided with a longitudinal series of chambers, either segregated into discrete, partitioned pockets or otherwise, which can be aligned with their corresponding ports upon proper rotation of the inner tube. Certain of such samplers have also provided for the discharge of the samples thus obtained through the open, normally upper end thereof.

SUMMARY OF THE PRESENT INVENTION

A primary objective, therefore, of the present invention is to provide a grain sampling probe that avoids the complexity, costs, mechanical unreliability and unwieldiness of prior devices of this type and affords instead an easy-to-use, mechanically trouble-free, relatively low-cost and reliable sampling tool that satisfies the fundamental needs of most users of such tools.

In furtherance of this objective, the present invention contemplates the use of a tubular body as the primary component thereof, such body having a laterally disposed port adjacent its lower end for admitting grain into an interior chamber when the probe is thrust down into the grain supply. A sleeve-like valve cover slides freely along the tube in a longitudinal direction between an upper position which closes the port and a lower position opening the port. Actuation of the valve cover is provided by the grain itself which, when the probe is thrust down into the grain, forces the valve cover up to close the port and, on the other hand, when the probe is pulled upwardly to remove it from the grain, forces the cover downwardly away from the port to uncover the same. Once the probe is removed from the grain, the probe may be inverted so as to pour the sample out the open upper end of the tube into an awaiting receptacle.

BRIEF DESCRIPTION OF THE DRAWING

FIG. 1 is an elevational view of a grain probe constructed in accordance with the principles of the present invention;

FIG. 2 is a fragmentary, enlarged elevational view thereof showing the sleeve-like valve cover thereof exposing the grain entry port as in FIG. 1;

FIG. 3 is a top end elevational view of the probe;

FIG. 4 is a fragmentary, longitudinal, cross-sectional view of the probe with the valve cover disposed in its port-closing position;

FIG. 5 is a transverse, cross-sectional view of the probe with the port closed as in FIG. 4 and taken along line 5—5 thereof;

FIG. 6 is a fragmentary, diagrammatic view of the probe during use showing the way in which the valve cover closes the port during insertion of the probe into the grain; and FIG. 7 is a view similar to FIG. 6 but showing the way in which the valve cover exposes the port as the probe is withdrawn from the grain.

DETAILED DESCRIPTION

With initial attention to the lower end of the probe 10, it may be seen that the latter includes an elongated hollow body in the nature of a tube 12 provided with an internal sample-receiving chamber 14. A lateral port 16 in the tube 12 communicates the chamber 14 with the exterior of the tube 12, such port 16 being spaced a short distance above the lower end 18 of tube 12. A downwardly tapering nose 20 secured to the lower end 18 of tube 12 facilitates penetration of the probe 10 down into a supply of grain, and such nose 20 is provided with an upwardly facing socket 22 at its upper end which includes a cavity 24 encircled by an annular rim 26. Cavity 24 is sized to matingly receive the lower end 18 of tube 12, and the latter is suitably fixedly secured to the nose 20 via welding, pop rivets or the like.

A valve cover in the nature of a sleeve 28 is slidably received on the tube 12 for longitudinal shifting movement between the lower extreme position of FIG. 2 and the upper extreme position of FIG. 4. An upper stop 30 projecting outwardly from the tube 12 slightly above the port 16 and in the path of travel of the sleeve 28 determines the limit of upward shifting movement of the sleeve 28, and in such position, the sleeve 28 fully closes the port 16 as shown in FIG. 4. On the other hand, the rim 26 of the nose 20 forms an outwardly projecting shoulder from the tube 12 so as to define a lower stop in the path of travel of the sleeve 28 spaced longitudinally below the upper stop 30. While the upper stop 30 is disposed for engagement with the upper edge 34 of sleeve 28, the rim 26 is disposed for limiting engagement with the lower edge 36 of sleeve 28 as shown in FIG. 2, in which position the sleeve 28 fully opens and exposes the port 16. The sleeve 28 is imperforate throughout its entire expanse such that, when sleeve 28 is in the port-closing position of FIG. 4, port 16 is indeed closed regardless of the rotative position of sleeve 28 on tube 12, it thus being unnecessary to provide guidance structure which would prevent rotation of the sleeve 28 and limit the latter solely to rectilinear movement.

The tube 12 extends substantially upwardly beyond the port 16 and thus forms a handle that facilitates use of the probe 10. For convenience and ease of manufacture, it is contemplated that the sample-receiving area of the probe 10 and the handle area thereof will comprise integrally connected portions of a common tube 10 as illustrated, although it is to be understood that certain aspects of the present invention in connection with a lateral port 16, the valve covering sleeve 28, etc. are significant in their own right regardless of the particular configuration of a handle that might be incorporated into the design to facilitate use.

In other respects, however, it will be apparent that the characteristics of the lower, grain-collecting portion of the probe 10 combine with the characteristics of the upper handle portion thereof to provide an overall improved tool. In this regard, the fact that the probe 10 is basically tubular throughout its entire length, save for being closed at its lower end by the nose 20, contributes to ease of use in that the tool may be relatively light weight and that a sample collected within the chamber 14 may be easily and accurately poured into an awaiting receptacle or the like through the outlet 38 across the upper end of the tube 10.

Use of the probe 10 should be apparent from the foregoing description and by examination of FIGS. 6 and 7. Although the valve sleeve 28 might be resting with its lower edge 36 upon the rim 26 prior to the probe 10 being inserted into a supply of grain, once the probe 10 is indeed thrust downwardly into the grain supply denoted by the numeral 40 in FIG. 6, the resistance of the grain surrounding the probe 10 immediately slides the sleeve 28 up against the upper stop 30 so as to close the port 16 throughout continued downward thrusting of the probe 10 to the selected depth for sampling purposes.

When the probe 10 has been inserted to the desired depth, an upward pull on the probe 10 as illustrated in FIG. 7 will immediately cause the surrounding grain to pull the sleeve 28 down against the rim 26 so as to open and expose the port 16. Grain surrounding the port 16 at its particular depth flows into the chamber 14, filling the same to the level of the port 16. Thus, withdrawal of the probe 10 may be continued with the assurance that a sample at the desired depth has been obtained.

After the probe 10 has been fully withdrawn as above mentioned, the probe 10 may simply be inverted and the sample poured from the probe 10 along the tube 12 and out the outlet 38 into an awaiting receptacle or the like.

It should thus be apparent that the sampling probe of the present invention is quite easy to use and yet, by the same token, is quite capable of carrying out its intended function. Its fully self-contained nature means there is no risk of losing one or more components thereof either during use or storage as has not been at all uncommon in prior devices of this class. Furthermore, its minimization of moving parts compared to prior devices correspondingly reduces the likelihood of mechanical failure due to unskilled use or otherwise, and additionally helps maintain the cost of manufacture at a satisfactorily low level that will be attractive to prospective purchasers.

I claim:

1. A grain sampling probe comprising:
   an elongated, hollow body provided with an internal chamber;
   means at the normally lower end of said body for facilitating penetration of the body in a longitudinal direction into a supply of grain to be sampled;
   a lateral port in said body communicating said chamber with the exterior of the body;
   a valve cover shiftable longitudinally along said body for opening and closing said port;
   a first stop on the body in the path of travel of said valve cover for preventing said shifting of the valve cover in one direction beyond a closing position wherein the valve cover closes said port as the body is inserted into the grain supply; and
   a second stop on the body spaced longitudinally from said first stop and disposed in the path of travel of said valve cover for preventing said shifting of the valve cover in the opposite direction beyond an opening position wherein the valve cover opens said port as the body is withdrawn from the grain supply, thereby permitting a sample of grain to enter said port and collect in said chamber,
   said body comprising a tube,
   said penetration facilitating means comprising a tapered nose closing the normally lower end of said tube and provided with a radially outwardly projecting shoulder defining said second stop.

2. A grain sampling probe as claimed in claim 1, wherein said valve cover comprises a tubular sleeve slidably receiving said tube 3. A grain sampling probe as claimed in claim 2, wherein said sleeve is freely rotatable around said tube and is laterally imperforate for maintaining said port closed when the valve cover is at said closing position thereof regardless of the rotative disposition of said valve cover on the tube.

4. A grain sampling probe as claimed in claim 1, wherein said nose is provided with a socket fixedly receiving said lower end of the tube, said socket having a cavity for the tube and an annular rim around said cavity presenting said shoulder.

5. A grain sampling probe comprising:
   an elongated, hollow body provided with an internal chamber;
   means at the normally lower end of said body for facilitating penetration of the body in a longitudinal direction into a supply of grain to be sampled;
   a lateral port in said body communicating said chamber with the exterior of the body;
   a valve cover shiftable longitudinally along said body for opening and closing said port;
   a first stop on the body in the path of travel of said valve cover for preventing said shifting of the valve cover in one direction beyond a closing position wherein the valve cover closes said port as the body is inserted into the grain supply;
   a second stop on the body spaced longitudinally from said first stop and disposed in the path of travel of said valve cover for preventing said shifting of the valve cover in the opposite direction beyond an opening position wherein the valve cover opens said port as the body is withdrawn from the grain supply, thereby permitting a sample of grain to enter said port and collect in said chamber; and
a handle rigidly joined to said body and extending longitudinally therefrom away from said lower end thereof,
said body and said handle comprising integrally connected, longitudinally aligned portions of a common tube,
said tube having an outlet adjacent the normally upper end thereof for emptying a sample from the same,
said outlet extending across the normally upper end of the tube on the longitudinal axis thereof,
said penetration facilitating means comprising a tapered nose closing the normally lower end of the tube, said nose being provided with a socket fixedly receiving said lower end of the tube, said socket including a cavity for the tube and an annular rim around the cavity defining said second stop.

* * * * *